United States Patent
Gao et al.

(10) Patent No.: US 9,462,969 B2
(45) Date of Patent: Oct. 11, 2016

(54) MICRONEEDLE

(75) Inventors: Feng Gao, Espoo (FI); Jyrki Kiihamäki, Espoo (FI); Ari Hokkanen, Espoo (FI); Päivi Heimala, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 13/265,290

(22) PCT Filed: Apr. 20, 2010

(86) PCT No.: PCT/FI2010/050318
§ 371 (c)(1),
(2), (4) Date: Nov. 18, 2011

(87) PCT Pub. No.: WO2010/122222
PCT Pub. Date: Oct. 28, 2010

(65) Prior Publication Data
US 2012/0058506 A1    Mar. 8, 2012

(30) Foreign Application Priority Data
Apr. 20, 2009 (FI) ................................. 20095433

(51) Int. Cl.
*A61M 5/32* (2006.01)
*A61B 5/15* (2006.01)
(Continued)

(52) U.S. Cl.
CPC .......... *A61B 5/1411* (2013.01); *A61B 5/14514* (2013.01); *A61B 5/150022* (2013.01);
(Continued)

(58) Field of Classification Search
CPC ............ A61M 2037/0023; A61M 2037/0046; A61M 203/0061
USPC ................................. 604/242, 117, 264, 272
See application file for complete search history.

(56) References Cited

U.S. PATENT DOCUMENTS 3,492,992 A * 2/1970 Kurtz ............................. 604/272
4,808,157 A * 2/1989 Coombs ......................... 604/44
(Continued)

FOREIGN PATENT DOCUMENTS

EP    1 652 551 A2    5/2006
EP    1 669 100 A1    6/2006
(Continued)

OTHER PUBLICATIONS

McAllister et al. PNAS; 2003, vol. 11, No. 24; pp. 13755-13760.*
(Continued)

*Primary Examiner* — Edelmira Bosques
(74) *Attorney, Agent, or Firm* — Seppo Laine Oy

(57) ABSTRACT

The application relates to microfluidic needles and their manufacturing methods. The microfluidic needle comprises an interface portion containing at least one fluid communication channel, an elongated needle portion (40) projecting away from the interface portion (44), the needle portion having a tip and sidewalls connecting the tip to the interface portion, and at least two microfluidic channels (43 A-B) within the needle portion in fluidic connection with the at least one communication channel, the microfluidic channels being at least partly oriented parallel to the elongated needle portion. According to the application, the microfluidic channels exit the needle portion at the sidewalls of the needle portion. The needle may be fabricated by ALD-assisted silicon micromachining. The needle can be used for injection and/or sampling fluids to/from tissue or individual cells.

17 Claims, 5 Drawing Sheets

(51) Int. Cl.
*A61B 5/151* (2006.01)
*A61M 37/00* (2006.01)
*A61B 5/145* (2006.01)

(52) U.S. Cl.
CPC ..... *A61B5/15142* (2013.01); *A61B 5/150282* (2013.01); *A61B 5/150419* (2013.01); *A61B 5/150435* (2013.01); *A61B 5/150511* (2013.01); *A61M 37/0015* (2013.01); *A61B 2562/0295* (2013.01); *A61M 2037/003* (2013.01); *A61M 2037/0053* (2013.01); *A61M 2037/0061* (2013.01)

(56) References Cited

U.S. PATENT DOCUMENTS

| | | | |
|---|---|---|---|
| 5,591,139 A * | 1/1997 | Lin et al. | 604/264 |
| 6,451,240 B1 * | 9/2002 | Sherman et al. | 264/504 |
| 6,678,556 B1 * | 1/2004 | Nolan et al. | 604/21 |
| 2003/0187394 A1 * | 10/2003 | Wilkinson et al. | 604/131 |
| 2003/0199812 A1 * | 10/2003 | Rosenberg | 604/47 |
| 2004/0164454 A1 | 8/2004 | Gartstein et al. | |
| 2006/0030812 A1 | 2/2006 | Golubovic-Liakopoulos et al. | |
| 2007/0185432 A1 | 8/2007 | Etheredge, III et al. | |
| 2007/0233016 A1 | 10/2007 | Kuo et al. | |
| 2007/0275521 A1 | 11/2007 | Fu | |
| 2009/0093776 A1 | 4/2009 | Yue et al. | |

FOREIGN PATENT DOCUMENTS

| | | |
|---|---|---|
| EP | 1967581 A1 | 9/2008 |
| EP | 1 985 579 A2 | 10/2008 |
| KR | 2002-0081743 A | 10/2002 |
| WO | WO 00/16833 A1 | 3/2000 |
| WO | WO 00/74764 A1 | 12/2000 |
| WO | WO 03/015860 A1 | 2/2003 |
| WO | WO 2005/060621 A2 | 7/2005 |
| WO | WO 2006/025786 A1 | 3/2006 |
| WO | WO 2007/070004 A2 | 6/2007 |
| WO | WO 2008/027011 A1 | 3/2008 |
| WO | WO 2008/028087 A2 | 3/2008 |

OTHER PUBLICATIONS

International Search Report, PCT/FI2010/050318, Nov. 3, 2010.
Lye W-K et al., "Microsystems for Drug and Gene Delivery", Proceedings of the IEEE, IEEE. New York, US LNKD—DOI:10.1109/JPROC.2003.820542, vol. 92, No. 1, Jan. 1, 2004, pp. 56-75, XP011105256.
Office Action for European Patent Application No. 10718626.4, dated Oct. 26, 2012.

* cited by examiner

Fig. 1A                    Fig. 1B

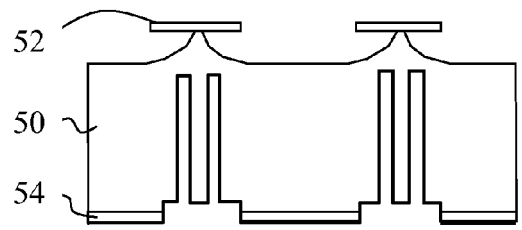
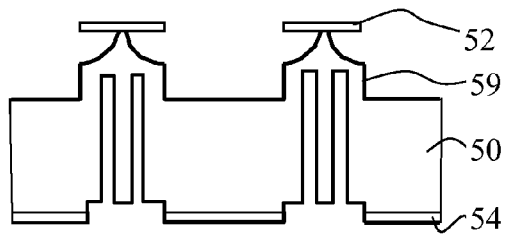
Fig. 5g                Fig. 5h
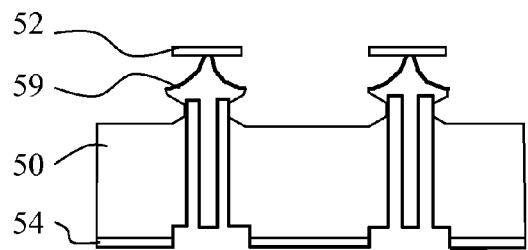
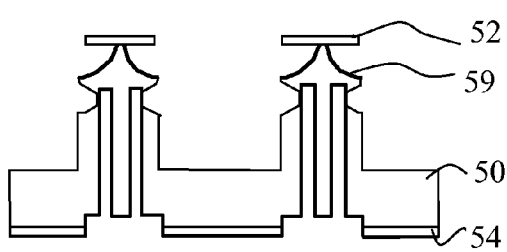
Fig. 5i                Fig. 5j
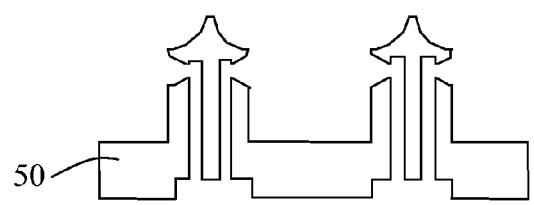
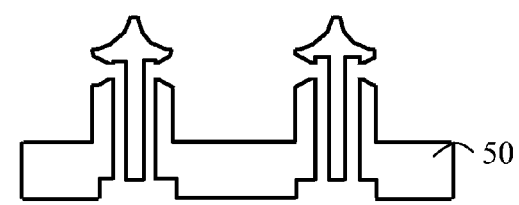
Fig. 5k                Fig. 5l

MICRONEEDLE

FIELD OF THE INVENTION

The invention relates to microfluidic needles according to the preamble of claim 1. Such needles can be used for injecting fluids to and/or sampling fluids from human or animal tissue or individual cells.

BACKGROUND OF THE INVENTION

Microfluidic needle devices generally comprise a microfluidic channel manufactured to silicon or polymer substrate. Conventional microneedles contain one single hole in one needle. To increase the throughput of fluid through the device or to provide parallel injection of several substances, there may be provided an array of microneedles. Microneedle arrays are known, for example, from US 2007/0233016, disclosing a device with a supporting pad and a plurality of microneedles having slant or concave tips. Also EP 1183064 discloses a microneedle array.

Microneedle arrays have the disadvantage that they take relatively much space on the substrate in relation to the throughput achieved. In addition, very local simultaneous injection and sampling of fluid is not possible.

WO 00/16833 discloses a surface-machined microneedles fabricated "horizontally" on a substrate and a multilumen microneedle having a plurality of microchannels. Such design is difficult to implement such that the microchannels would be ordered in two dimensional configuration.

KR 20020081743 discloses a single-crystal silicon microneedle which may have a plurality of individual microchannels, i.e., a so-called multiport microneedle. The microchannels are located parallel to each other and have their exits on a slanted tip of the needle.

EP 1967581 discloses CMOS-compatible microneedle structures. There is disclosed a microneedle structure wherein a microfluidic channel and filled conductor channel acting as a sensing or actuating electrode are integrated into a single needle.

US 2009/0093776 discloses microneedle structures in which the microchannel exits are located at least partly on a slanted surface of the needle, relatively wide and therefore accessible directly from the top of the needle. Such structure is prone to clogging and does not allow transport of fluids to/from to the vicinity of the tip of the needle.

EP 1652551 discloses completely different microneedle type, in which there are no inner microchannels at all, but the channels are formed as slanted groove open to the sides of the microneedle along the whole length of the needle. Also such structure is prone to clogging.

One-channel needles are disclosed in EP 1669100, WO 2003/015860 and WO 2008/027011.

The approaches referred to above have disadvantages, one of which is the clogging of the needles. As the size of the microfluidic channels is reduced, as is necessary in the case of multichannel needles, even smaller particles will stick to the channels and prevent fluid flow fully or partially. In addition, as the exits of the needle are located very close to each other, simultaneous injection and sampling are directed to a very local area, whereby sampling may not give reliable results in certain applications.

SUMMARY OF THE INVENTION

It is an aim of the invention to overcome at least some of the problems of prior art and to provide an improved multiport microneedle. A particular aim of the invention is to provide a non-clogging multiport microneedle.

The above problems are solved by the aspects of the invention as defined in the independent claims.

The microneedle comprises an interface portion containing at least one fluid communication channel, i.e., a fluid feed/discharge channel, and an elongated needle portion projecting away from the interface portion and having at least two micro fluidic channels therein. The micro fluidic channels are in fluidic connection with the at least one fluid communication channel of the interface portion. According to the invention, the microfluidic channels exit through the sidewall of the needle portion, preferably on different sides thereof. In other words, the microfluidic channels have their inlet/outlet ports not at the tip of the needle but at a distance from it and the inlet/outlet of fluid to/from the needle does not occur parallel to the needle portion but at an angle, preferably about right angle, with respect to the needle portion. Preferably, the inlet/outlet ports are, however, located in the immediate vicinity of the tip of the needle portion.

The clogging problem can be particularly efficiently avoided by a configuration in which the micro fluidic channels run parallel to each other from the at least one fluid communication channel to the vicinity of the tip of the needle portion and turn perpendicularly to the needle portion to exit the needle portion at the sidewalls of the needle portion and on different sides thereof.

In particular, the present multiport microneedle may have a plurality of individual microfluidic connections to one single needle. That is, there are at least two separate feed/discharge channels in the interface portion. Thus, it is possible to use the microfluidic channels of the microneedle separately and simultaneously for injection and/or sampling. In other words, the needle can be used for injecting simultaneously different fluids, for sampling fluid directly to two or more destinations or for simultaneous injection and sampling of fluid.

The microneedle of the present kind in preferably fabricated by silicon micromachining and it may constitute a monolithic or single-crystal entity. In the method according to the invention, an isotropic etching step is provided for manufacturing the micro fluidic channels opening at the sidewalls of the needle. Preferably, the manufacturing process comprises

- providing a silicon wafer having two opposite surfaces,
- etching the silicon wafer anisotropically on first surface thereof for manufacturing a microfluidic channel having a predefined depth,
- etching the silicon wafer at least partly anisotropically on second surface thereof for manufacturing a needle portion having a predefined height around the microfluidic channel, and
- before the needle portion is given its final height, etching the silicon wafer isotropically such that the micro fluidic channels are opened from the sides of the needle portion.

In particular, the isotropic etching may be carried out very locally to desired positions by using an atomic layer deposited (ALD) mask layer, such as an $Al_2O_3$ layer, as will be described in more detail later.

The present microneedle can be used with any kinds of fluid substances, mainly liquids and gases.

Microneedles of the present kind may also be arranged into an array allowing processing of larger fluid volumes.

The invention provides significant advantages. Multiport microneedle has possibility to do simultaneous multiport injection and/or sampling with one single needle. It is, for example, possible to inject heparin to prevent blood coagulation while simultaneously sampling blood through the other port in the same needle. As the microchannels are located close to each other, very localized sampling/injection is achieved.

The transverse orientation of the exit ports of the microfluidic channels of the needle ensures that the channels are not clogged when the needle is inserted into tissue. This is because the exit ports are not accessible directly from the top of the needle (in the direction of the needle portion/microfluidic channels).

The present invention provides a unique technique for manufacturing needles with a plurality of internal multi-channels and transversely oriented exit ports.

Moreover, production of silicon microneedles is possible in standard MEMS foundries, in particular using silicon wafer processing. In particular, combined with ALD technology, the transverse channel exit configuration can be conveniently produced.

Application areas of the invention include blood analysis (e.g. CRP, Cardiac Markers: Troponin, Myoglobin, glucose testing, and drug injection (e.g. insulin) and cell research (e.g. microinjection in drug discovery). A specific application area, in which the microneedle of the present kind offers significant advantages, is the manipulation of single cells. This in because the present multichannel microneedle can be brought into a cell in a non-clogging manner and various measurements can be performed with it. In vivo, ex vivo or in vitro experiments are possible. Of particular importance are experiments, where the single microneedle is used for both injecting fluid to the cell and sampling of fluid from the same cell. Thus, the invention provides a novel kind of microneedle for pipetting fluids to and/or from an individual cell.

Next, the embodiments of the invention will be described more closely with the aid of the drawings.

BRIEF DESCRIPTION OF DRAWINGS

FIGS. 1A-1C show a microneedle which can be included in the present device in a perspective view, cross-sectional side view and bottom view, respectively.

FIGS. 5a-5l show an exemplary silicon processing scheme in a step-by-step manner for the manufacture of microneedles according to the invention.

DETAILED DESCRIPTION OF EMBODIMENTS

Figure 1C:
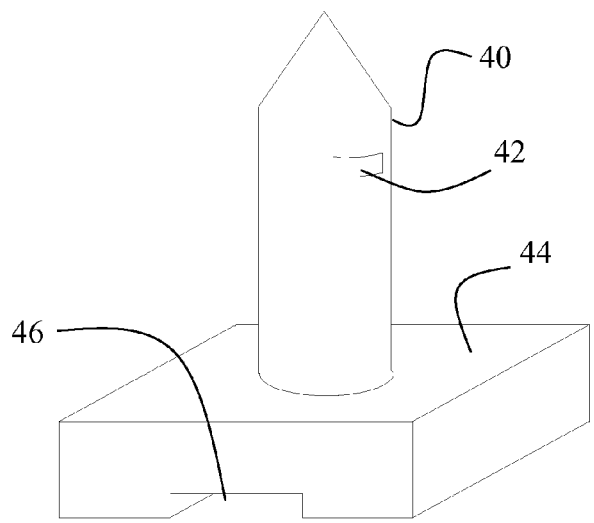
Figure 1C:
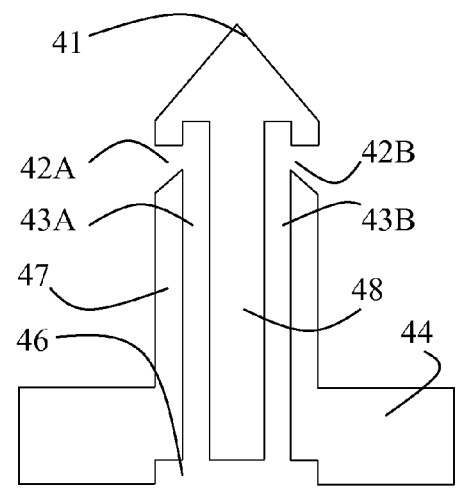
Figure 1C:
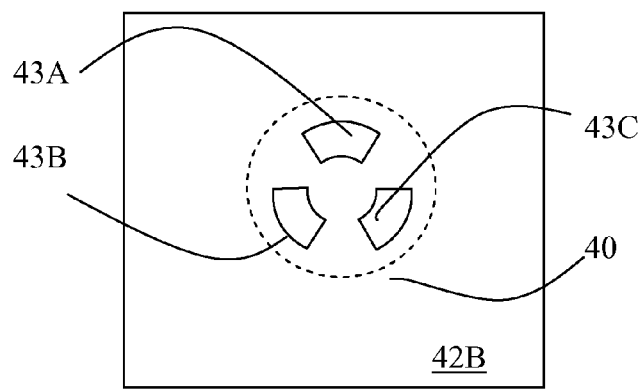
Figure 2:
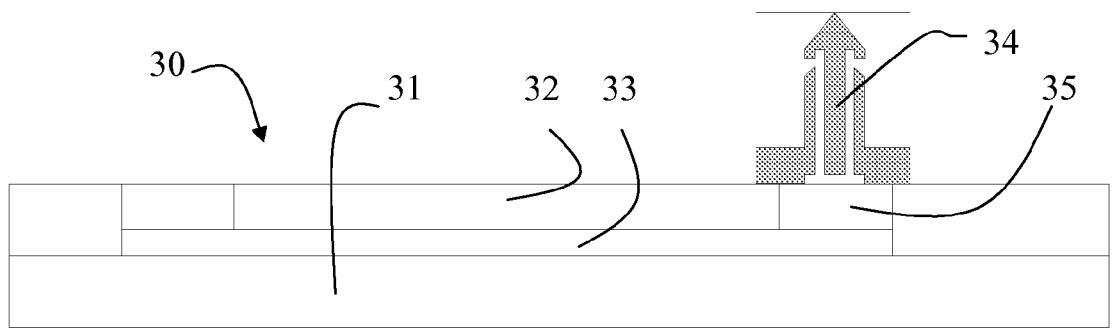
FIG. 2 shows in a cross-sectional view a polymer body containing a microfluidic needle according to one embodiment of the invention.

FIGS. 1A-1C show exemplary microneedle structures in different views. The microneedle comprises a needle portion 40 and a mounting/interface portion 44, which can be used for mounting the microneedle on a substrate. The needle portion is circular in cross section and has constant diameter, apart from the tip portion, which is tapering. The interface portion 44 comprises a silicon wafer and a feeding channel 46. The feeding channel 46 is connected to one or more capillary microfluidic channels 43A-43C contained within the needle portion 40 and being parallel therewith. The microfluidic channels 43A-43C are defined by wall portions 47, 48 of the needle portion.

The wall portions 47 and 48 of the needle portion are exterior sidewalls of the needle portion.

Each of the capillary channels is provided with an inlet/outlet 42A, 42B, which are preferably located on the side of the needle portion 40. The needle portion 40 comprises a tapering portion extending from the vicinity of the inlets/outlets 42A, 42B towards the tip 41 of the microneedle. The cross-section of the individual capillary channels 43A-43C may be, for example, arch-like as shown in FIG. 1C, rectangular, circular or of any other suitable shape.

Generally, the diameter of the needle portion may be 1-300 µm and the height 5-600 µm, in particular 100-600 µm. The thickness of the mounting/interface portion is typically 100-400 µm.

According to one embodiment, suitable for example for body fluid (such as blood) sampling applications, the diameter of the needle portion is 100-250 µm, in particular 100-200 µm, the height of the needle portion being typically 100-600 µm, in particular 200-400 µm. In a multi-needle component the center-to-center separation between individual needles may vary between 200 and 800 µm. The width of an individual capillary channel in the radial direction of the needle portion may be 20-80 µm, in particular 30-60 µm. For blood sampling, it is preferable that the cross-sectional area of each capillary channel is as least 400 µm$^2$, allowing the various types of blood cells to flow through it.

For single cell manipulation applications, the diameter of the needle portion must generally be less than 100 µm, in particular 2-100 µm, the height of the needle portion can be for example 5-400 µm. The width of an individual capillary channel in the radial direction of the needle portion may be, for example, 1-30 µm. The cross-sectional area of each capillary channel may be, for example, 3-1000 µm$^2$.

As briefly mentioned above, there may also be separate feed/discharge channels for two or more, preferably each, microfluidic channels 43A-43C of the needle portion for allowing individual fluid feed or injection to/from the microneedle. In this case, the fluid feed/discharge channels of the interface portion 44 are respectively designed such that they can be individually connected with separate microchannels of a substrate. In particular, the interface portion may comprise at least two fluid communication channels which can be individually fed with fluid at different locations of the interface portion 44, the communication channels being individually connected with microfluidic channels of the needle portion. Access to the fluid communication channels may be provided on lateral sides or underside thereof, depending on the intended mounting scheme of the microneedle.

In addition to or instead of the individual fluid communication channels, the interface portion may comprise a fluid communication channel in fluidic connection with two or more microfluidic channels of the needle portion. Thus, a single injection feed can be directed to two or more outlets of the needle or sample feeds from two or more inlets of the needle portion may be combined within the microneedle.

According to one embodiment, the interface portion contains at least one fluid communication channel which can be fed with fluid perpendicularly to the direction of the needle portion when the microneedle is mounted on a substrate. The channel may be half-open as shown in FIGS. 1A and 1B, whereby the substrate closes the channel from the underside. Alternatively, the channel may be a closed (on other sides than the ends of the channel), leaving only the end of the channel visible. According to one embodiment, the microneedle can only be fed through channel ends at the bottom of the interface portion 44.

According to a preferred embodiment, the microfluidic channels exit the needle portion at different sides of the needle portion. In particular, they may exit in symmetric configuration, as observed in a plane perpendicular to the general direction of the needle portion.

The needle portion may comprise, for example, 2-10 microfluidic channels. In a typical configuration, the number of channels is two, three, four, five or six micro fluidic channels.

According to a preferred embodiment, the microfluidic channels of the needle portion run parallel to each other to the vicinity of the tip of the needle portion and then turn transversely to the direction to the needle portion to exit the needle portion on different sides thereof.

Microneedles of the present kind can be arranged as an integral unit so as to form a multi-needle element, in particular a microneedle array. In such array there are a plurality of needle portions projecting away from a common interface portion. The microfluidic channels of the needle portions may be connected all to a single fluid communication channel of the interface portion, allowing delivery of the same fluid through all channels of the array, or in groups to separate fluid communications channels of the interface portion, allowing delivery of separate fluids in parallel through the channels of the array. The grouping can be freely designed. In typical configurations either the individual microchannels of the needles operate in parallel (each needle connected to at least two different fluid communications channels) or the individual needles operate in parallel (each needle connected to only one fluid communication channel, but there are at least two needles connected to different fluid communication channels). A combination of the above schemes is also possible.

Figure 4:
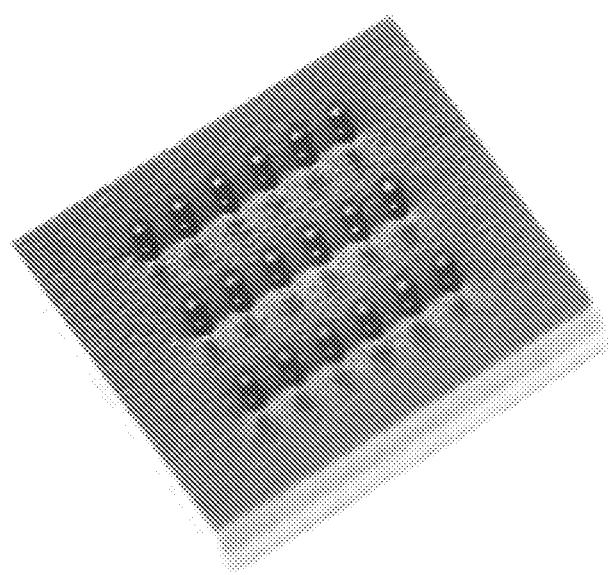
FIG. 4 is a photograph of a multi-needle microneedle chip.

A microneedle array may contain, for example, 2-64, or even more, typically 2-32, individual needles arranged in a regular or non-regular configuration. A photograph of a multi-needle microneedle component comprising 18 individual needles is shown in FIG. 4.

The microfluidic needle can be manufactured from silicon. In particular, it can be single-crystal silicon product.

According to one embodiment, the microneedle chip has an area of 4 mm$^2$ or less, in particular 2 mm$^2$ or less, most preferably 1 mm$^2$ or less. Thus, the consumption of silicon is minimized.

The microneedle can be manufactured by high-precision silicon or glass processing technologies known per se. One possible manufacturing process is described in detail below.

A microneedle of the present kind can be manufactured by silicon micromachining FIGS. 5*a*-5*l* illustrate the basic steps of one possible manufacturing process, in which two microneedles are manufactured next to each other on a wafer. It is to be noted that the scale of the figures is arbitrary and may change between individual figures for clarity reasons.

Figure 5A:
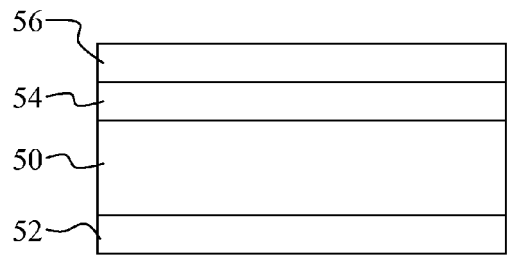
Figure 5B:
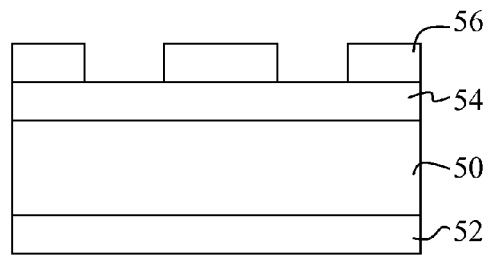
Figure 5C:
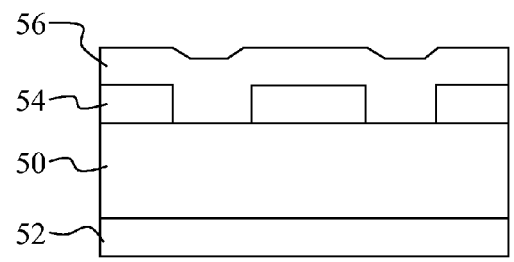
Figure 5D:
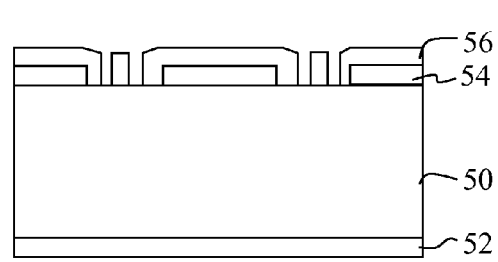
Figure 5E:
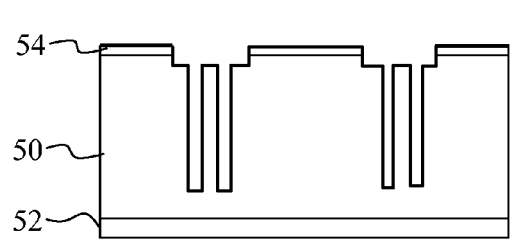
Figure 5F:
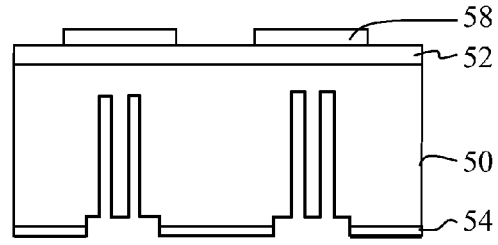

In the first step (FIG. 5*a*), a silicon wafer 50 is provided and silicon oxide SiO$_2$-layers 52 and 54 are provided on both surfaces thereof. Processing is begun with backside lithography (herein the "backside" is the side of the wafer eventually forming the mounting side of the needle). Thus, a resist coating layer 56 is provided on the backside of the wafer. For manufacturing the fluid feeding channel, the resist layer 56 is patterned to form a suitable mask (FIG. 5*b*). Oxide layer 54 is etched (using e.g. LAM rainbow 4520) and resist application, patterning and etching is continued in order to manufacture the feeding channel and vertical microfluidic channels inside the needle (FIGS. 5*c*-5*e*). When the microfluidic channels are in their target depth, a thin silicon oxide layer is grown thermally on the microfluidic channels (bold line in FIG. 5*e*).

Once the backside of the wafer is ready, processing is continued with front side lithography (i.e. on the needle tip side of the wafer). FIGS. 5*f*-5*l* show the wafer flipped around 180°. Resist layer 58 is applied and patterned to form a mask for the outline of the needle. After that, front side isotropic silicon etching is performed using, for example, Aviza deep silicon etcher, in order to give shape to the tip of the needle below the oxide and resist layers 52 and 58 (FIG. 5*g*). In the next step, the silicon wafer outside the needle portion is anisotropically (vertically) etched such that the surface of the wafer is slightly below the bottoms of the capillary channels etched earlier (FIG. 5*h*). Onto the etched surface is deposited an Al$_2$O$_3$ layer 59 using the atomic layer deposition (ALD) method. The thickness of the ALD layer 59 is typically 20-50 nm. After that, the horizontal sections of the ALD layer 59 are removed by anisotropic etching (e.g. LAM metal etcher). Once the Al$_2$O$_3$ is partially removed, silicon wafer is etched once again by isotropic etching such that the ends of the capillary channels are reached from the sides of the needle (FIG. 5*i*). After that, anisotropic etching is continued until the target height of the needle portions is achieved (FIG. 5*j*). Finally, undesired processing materials are removed for obtaining functional silicon microneedles (FIG. 5*k*). As a last step, the silicon surfaces can be oxidized (bolded lines in FIG. 5*l*) to ensure the hydrophilic properties of the microfluidic channels inside the needle.

In more general terms, the exit paths of the microfluidic channels can be formed such that
  isotropic silicon etching is performed on the second surface of the silicon wafer to give shape to the tip of the needle under the oxide mask
  the silicon wafer is anisotropically etched on the second surface to a depth corresponding, preferably slightly overlapping with the depth of the microfluidic channel,
  an etch mask layer (e.g. the atomic layer deposited Al$_2$O$_3$ layer) is provided on the sides of the semi-finished needle portion thus formed,
  second anisotropic etching is performed to open the microfluidic channels, and
  the anisotropic etching on the second surface of the silicon wafer is continued to give the needle portion its final height.

For practical reasons it is convenient to provide the etch resist layer on essentially the whole second surface of the silicon wafer, and to remove the etch resist layer from vertical portions of the surface (i.e. surfaces not forming sides of the needle portion). Thus, the isotropic etching may proceed sideways towards the microfluidic channels formed from the other surface of the wafer.

Figure 3:
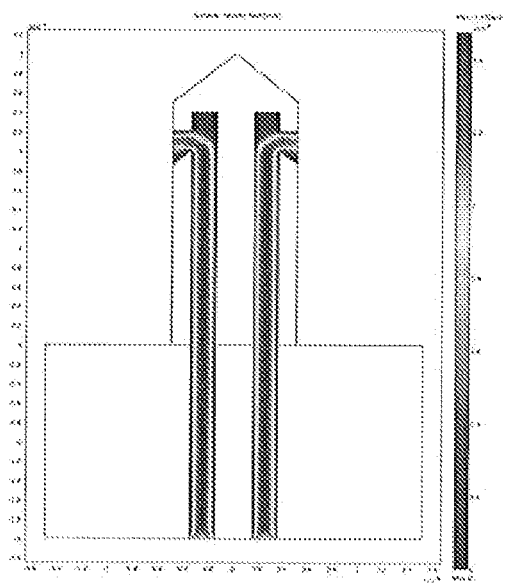
FIG. 3 shows calculated fluid pathways in a microneedle according to one embodiment of the invention.

As can be seen from the simulated fluid flow model show in FIG. 3, the fluid flow through a microneedle of the present kind is even and, in particular, not significantly disturbed by the potential additional cavities in the vicinity of the exit ports of the needle caused by the micromachining process.

According to one embodiment, the needle structure may comprise a second silicon layer on the backside i.e. interface side thereof, the second layer forming part of the interface portion of the needle. Such layer is integrally joined with the first silicon entity containing the needle portion and part of the interface portion, typically at wafer level, i.e., before cutting the needle from the wafer. The second layer contains vias connected to ends of the fluid channels fabricated into the first entity. The distance of the ends of individual fluid channels at the final interface surface is typically larger than the distance of the fluid channels at the fluid channels at the joining plane of the silicon layers. Thus, by this arrangement it is possible to extend the distance between separate channel ends to e.g. 0.5-1 mm and to provide easier access to the individual microchannels of the needle from the chip body the needle is mounted on. This is of particular importance if the chip body is made of plastic having inferior processing resolution compared to silicon. In particular, this arrangement may provide advantages in the case of multichannel microneedles having a diameter less than 200 µm, in particular less than 100 µm, as the distance between individual capillaries in the needle is short.

In the implementation of point of care devices, means for taking blood sample painlessly and automatically is the most critical component. A silicon microneedle of the present kind offers a convenient solution to this problem. As the needle can be integrated into functional lab-on-a-chip devices, rapid sample analysis is possible. In particular, the above-described heterogeneously integrated multi-element silicon-plastic (Siptic) point of care device in beneficial because of its low manufacturing costs and accuracy. In an exemplary sampling and analysis process, blood is taken using a silicon-based microneedle mounted on a polymer chip. The blood in conveyed directly from the needle through a microchannel of the body to an analysis element also mounted on the polymer chip. The analysis element contains means for analyzing a particular property of the blood sample, for example, glucose, haemoglobin or lactic acid content. The reading of the analysis element may further be electrically transferred to a computing device.

The invention claimed is:

1. A microfluidic needle comprising:
   an interface portion containing at least two fluid communication channels;
   an elongated needle portion projecting away from the interface portion, the needle portion having a tapering tip portion, connected to an exterior sidewall connecting the tip portion to the interface portion, the exterior sidewall extending perpendicularly from the interface portion; and
   at least two microfluidic channels, being in fluidic and individual connection with one of the at least two communication channels, and extending from the interface portion toward the tip within the needle portion, wherein
   the at least two microfluidic channels turn perpendicularly within the needle portion so that each of the at least two microfluidic channels exits only at the sidewall extending perpendicularly from the interface portion on different sides of the top half of the needle portion under the tip so as to prevent clogging.

2. The microfluidic needle according to claim 1, wherein the interface portion comprises at least two fluid communication channels which can be individually fed with fluid.

3. The microfluidic needle according to claim 1, wherein the at least one fluid communication channel of the interface portion is in fluidic connection with one or more of the at least two microfluidic channels of the needle portion.

4. The microfluidic needle according to claim 1, wherein the interface portion is mountable to a surface such that one of the at least two fluid communication channels can be fed with fluid perpendicularly to the direction of the needle portion.

5. The microfluidic needle according to claim 1, wherein it is manufactured from silicon.

6. The microfluidic needle according to claim 1, wherein the microfluidic channels exit the needle portion at different sides of the needle portion in symmetric configuration.

7. The microfluidic needle according to claim 1, wherein there are two, three, four, five or six microfluidic channels in the needle portion.

8. The microfluidic needle according to claim 1, wherein the needle portion is generally circular in cross-section.

9. The microfluidic needle according to claim 1, wherein the height of the needle portion is 200-400 µm, and the width of the microfluidic channels in the radial direction of the needle portion is 2-80 µm.

10. The microfluidic needle according to claim 9, wherein the width of the microfluidic channels in the radial direction of the needle portion is 5-60 µm.

11. The microfluidic needle according to claim 1,
    wherein a diameter of the needle portion is 1-250 µm,
    a height of the needle portion is 5-600 µm, and
    a width of the microfluidic channels in the radial direction of the needle portion is 2-80 µm.

12. The microfluidic needle according to claim 1, wherein the at least two microfluidic channels are separated from each other.

13. The microfluidic needle according to claim 1, wherein the elongated needle portion has a circular cross section of constant diameter, apart from the tapering tip portion.

14. A microneedle array comprising a plurality of microfluidic needles having:
    an interface portion containing at least two fluid communication channels;
    an elongated needle portion projecting away from the interface portion, the needle portion having a tapering tip portion, connected to an exterior sidewall connecting the tip portion to the interface portion, the exterior sidewall extending perpendicularly from the interface portion; and
    at least two microfluidic channels, being in fluidic and individual connection with one of the at least two communication channels, and extending from the interface portion toward the tip within the needle portion, wherein
    the at least two microfluidic channels turn perpendicularly within the needle portion so that each of the at least two microfluidic channels exits only at the sidewall extending perpendicularly from the interface portion on different sides of the top half of the needle portion under the tip so as to prevent clogging and
    wherein the plurality of needles have a common interface portion.

15. The microneedle array according to claim 14, wherein at least one of the at least two communication channels of the common interface portion is in fluidic connection with the microfluidic channels of two or more of the microfluidic needles.

16. A method of using a microneedle, comprising:
    providing a microneedle having an interface portion containing at least two fluid communication channels; an elongated needle portion projecting away from the interface portion, the needle portion having a tapering tip portion, connected to an exterior sidewall connecting the tip to the interface portion, the exterior sidewall extending perpendicularly from the interface portion; and at least two microfluidic channels, being in fluidic and individual connection with one of the at least two communication channels, and extending from the interface portion toward the tip within the needle portion, wherein the at least two microfluidic channels turn perpendicularly within the needle portion so that each of the at least two microfluidic channels exits only at the sidewall extending perpendicularly from the interface portion on different sides of the top half of the needle portion under the tip so as to prevent clogging; and pipetting fluids at least one of: to an individual cell through the microneedle and from an individual cell through the microneedle.

17. The method according to claim 16, wherein said pipetting is non-therapeutic or takes place ex vivo or in vitro.

* * * * *